(12) United States Patent
Havel et al.

(10) Patent No.: US 10,695,026 B2
(45) Date of Patent: Jun. 30, 2020

(54) DEVICE FOR THREE-DIMENSIONAL, INTERNAL ULTRASOUND WITH ROTATING TRANSDUCER AND ROTATING REFLECTOR

(71) Applicant: Muffin Incorporated, West Lafayette, IN (US)

(72) Inventors: William J. Havel, West Lafayette, IN (US); Peter S. McKinnis, Carrboro, NC (US)

(73) Assignee: Muffin Incorporated, West Lafayette, IN (US)

( * ) Notice: Subject to any disclaimer, the term of this patent is extended or adjusted under 35 U.S.C. 154(b) by 637 days.

(21) Appl. No.: 15/235,217

(22) Filed: Aug. 12, 2016

(65) Prior Publication Data
US 2017/0042505 A1  Feb. 16, 2017

Related U.S. Application Data

(60) Provisional application No. 62/203,978, filed on Aug. 12, 2015.

(51) Int. Cl.
*A61B 8/12* (2006.01)
*A61B 8/00* (2006.01)
(Continued)

(52) U.S. Cl.
CPC ............... *A61B 8/12* (2013.01); *A61B 8/445* (2013.01); *A61B 8/4461* (2013.01); *A61B 8/483* (2013.01);
(Continued)

(58) Field of Classification Search
CPC ......... A61B 8/12; A61B 8/483; A61B 8/4461; A61B 8/445; A61B 8/56; A61B 8/0891; A61B 8/13; G01S 15/8943; G10K 11/357
See application file for complete search history.

(56) References Cited

U.S. PATENT DOCUMENTS

| 4,834,102 A | 5/1989 | Schwarzchild et al. |
| 5,095,911 A * | 3/1992 | Pomeranz ............... A61B 8/12 600/463 |

(Continued)

FOREIGN PATENT DOCUMENTS

| JP | H05 154150 A | 6/1993 |
| JP | 2004/129697 | 4/2004 |

(Continued)

OTHER PUBLICATIONS

International Application No. PCT/2016/046706 International Search Report and Written Opinion, dated Oct. 28, 2016.

(Continued)

*Primary Examiner* — Angela M Hoffa
*Assistant Examiner* — Helene Bor
(74) *Attorney, Agent, or Firm* — Woodard, Emhardt, Henry, Reeves & Wagner, LLP (57) ABSTRACT

Devices and methods for obtaining a real-time, three-dimensional image of a body part, particularly a blood vessel. A catheter has a chamber in its tip. The chamber contains an ultrasound transducer and reflector which generally face each other and rotate about a common axis. The transducer element on the transducer and the reflective face on the reflector are both tilted off-axis. The difference in angular velocity generally creates a phase shift between the transducer and the reflective face. The phase shift allows the transducer and the reflective face to actively scan a three-dimensional volume that is generally bounded interiorly by a hyperboloid and exteriorly by the effective range of the ultrasound beam. The transducer and reflector may rotate at constant speeds or nonconstant speeds as well in the same direction or in opposite directions.

29 Claims, 6 Drawing Sheets

(51) Int. Cl.
*A61B 8/08* (2006.01)
*A61B 8/13* (2006.01)
*G10K 11/35* (2006.01)
*G01S 15/89* (2006.01)

(52) U.S. Cl.
CPC .............. *A61B 8/0891* (2013.01); *A61B 8/13* (2013.01); *A61B 8/56* (2013.01); *G01S 15/8943* (2013.01); *G10K 11/357* (2013.01)

(56) References Cited

U.S. PATENT DOCUMENTS

| | | | |
|---|---|---|---|
| 5,176,141 A | 1/1993 | Bom et al. | |
| 5,313,950 A * | 5/1994 | Ishikawa | A61B 8/12 600/459 |
| 5,377,682 A | 1/1995 | Ueno et al. | |
| 5,377,685 A | 1/1995 | Kazi et al. | |
| 5,471,988 A * | 12/1995 | Fujio | A61B 8/12 600/439 |
| 5,606,975 A * | 3/1997 | Liang | A61B 8/12 600/437 |
| 6,200,269 B1 | 3/2001 | Lin et al. | |
| 6,371,915 B1 | 4/2002 | Koger et al. | |
| 6,607,502 B1 | 6/2003 | Maguire et al. | |
| 6,599,288 B2 | 7/2003 | Maguire et al. | |
| 7,798,971 B2 | 9/2010 | Flesch et al. | |
| 8,206,307 B2 | 6/2012 | Barnard et al. | |
| 2002/0082503 A1 | 6/2002 | Chardrasekaran et al. | |
| 2002/0087083 A1 | 7/2002 | Nix et al. | |
| 2005/0283080 A1 | 12/2005 | Nita et al. | |
| 2006/0030797 A1 | 2/2006 | Zhou et al. | |
| 2006/0173348 A1 | 5/2006 | WIlser et al. | |
| 2007/0038114 A1 | 2/2007 | Couvillon | |
| 2007/0149917 A1 | 6/2007 | Bennett et al. | |
| 2007/0239010 A1 | 10/2007 | Johnson | |
| 2008/0097403 A1 | 4/2008 | Donaldson et al. | |
| 2008/0177183 A1 | 7/2008 | Courtney et al. | |
| 2008/0221506 A1 | 9/2008 | Rodriguez et al. | |
| 2009/0030312 A1 | 1/2009 | Hadjicostis | |
| 2009/0156941 A1 * | 6/2009 | Moore | A61B 5/02007 600/467 |
| 2009/0306518 A1 | 12/2009 | Kurse et al. | |
| 2010/0036258 A1 | 2/2010 | Dietz et al. | |
| 2010/0160788 A1 | 6/2010 | Davies et al. | |
| 2010/0234736 A1 | 9/2010 | Corl | |
| 2010/0249601 A1 | 9/2010 | Courtney | |
| 2010/0249602 A1 | 9/2010 | Buckley et al. | |
| 2010/0249604 A1 | 9/2010 | Hastings et al. | |
| 2011/0021924 A1 | 1/2011 | Sethuraman et al. | |
| 2011/0071400 A1 * | 3/2011 | Hastings | A61B 8/12 600/467 |
| 2011/0071401 A1 | 3/2011 | Hastings et al. | |
| 2011/0166455 A1 | 7/2011 | Cully et al. | |
| 2011/0196286 A1 | 8/2011 | Robertson et al. | |
| 2011/0263986 A1 | 10/2011 | Park et al. | |
| 2011/0301508 A1 | 12/2011 | Sethuraman et al. | |
| 2012/0123271 A1 * | 5/2012 | Cai | A61B 8/06 600/454 |
| 2012/0172698 A1 | 7/2012 | Teo et al. | |
| 2012/0265070 A1 * | 10/2012 | Sliwa | A61B 8/085 600/439 |
| 2013/0269174 A1 * | 10/2013 | Park | A61B 8/12 29/594 |
| 2013/0303907 A1 | 11/2013 | Corl | |
| 2013/0345556 A1 | 12/2013 | Courtney et al. | |
| 2014/0078519 A1 * | 3/2014 | Steffey | G01S 7/4817 356/625 |
| 2014/0107490 A1 | 4/2014 | Fearnot et al. | |
| 2014/0107491 A1 | 4/2014 | Fearnot et al. | |
| 2014/0107492 A1 | 4/2014 | Zhou | |
| 2014/0194743 A1 * | 7/2014 | Havel | A61B 8/445 600/459 |
| 2015/0065884 A1 * | 3/2015 | Fukushima | A61B 8/12 600/459 |
| 2015/0066014 A1 * | 3/2015 | Sliwa | A61B 18/1492 606/34 |

FOREIGN PATENT DOCUMENTS

| | | |
|---|---|---|
| WO | WO 95/19143 A1 | 7/1995 |
| WO | WO 00/23125 A2 | 4/2000 |
| WO | WO 2012/061643 A1 | 5/2012 |
| WO | WO 2014/059292 A1 | 4/2014 |

OTHER PUBLICATIONS

International Search Report and Written Opinion issued in PCT/US2013/064570, dated Jan. 24, 2014.
International Search Report and Written Opinion issued in PCT/US2013/064579, dated Jan. 23, 2014.
International Search Report and Written Opinion issued in PCT/US2013/064606, dated Jan. 8, 2014.
International Search Report and Written Opinion issued in PCT/US2013/064611, dated Jan. 28, 2014.
International Search Report and Written Opinion issued in PCT/US2013/064618, dated Jan. 24, 2014.
International Search Report and Written Opinion issued in PCT/US2014/058269, dated Jan. 9, 2015, 17 pgs.

* cited by examiner

DEVICE FOR THREE-DIMENSIONAL, INTERNAL ULTRASOUND WITH ROTATING TRANSDUCER AND ROTATING REFLECTOR

This application claims the benefit of U.S. Provisional Patent Application Ser. No. 62/203,978, filed on Aug. 12, 2015, the entire disclosure of which is incorporated herein by reference.

The present disclosure concerns devices and methods for ultrasound use within the human body, including devices and methods for employing ultrasound to image the interior of vessels, such as blood vessels.

BACKGROUND

Conventional intravascular ultrasound (IVUS) systems scan a disk-shaped plane emanating radially from a rotating single-element transducer or array transducer mounted on or within the body of a catheter. The scan provides a two-dimensional image representing a cross-section of the vessel or body through which the catheter passes. The two-dimensional scan can provide useful diagnostic information regarding lumen diameter and can identify localized anatomy, but the limited field of view provides little navigation or overall anatomy information to the user. Navigational information might be useful, for example, for more complex tasks such as delivering or retrieving stents or other vascular devices. These procedures are currently and typically used under the guidance of fluoroscopy.

It is possible to render three-dimensional images using an IVUS catheter by performing a pull-back scan with the catheter. The procedure involves beginning a two-dimensional scan and then pulling the catheter through the target anatomy at a known rate of speed, rapidly taking multiple two-dimensional images along the way. The collected images are then compiled into a three-dimensional model. The model, however, is only an historical snapshot of the anatomy and does not provide real-time three-dimensional views.

As a result, there remains a need for accurate and efficient application of ultrasound in three dimensions along a substantial length of a vessel or other bodily area, for example to provide a physician with a real-time view along that length. There also remains a need for devices that can view a medical device and one or more tissues or tissue parts simultaneously, particularly in cases in which the device and tissue(s) could not have been imaged reliably in any two-dimensional plane.

SUMMARY

Among other things, the following is a general explanation of the devices and methods to use an ultrasound beam to obtain real-time, three-dimensional views inside the vascular system of the human body. In particular embodiments an apparatus includes an elongated tubular member with a chamber in its distal end (the end inserted into the vascular system of the patient). The chamber contains a rotating transducer that is generally pointed toward the distal end of the device, with the transducer element oriented slightly off-axis from residing within a perpendicular transverse plane relative to the axis about which the transducer rotates. The off-axis tilt causes the transducer to emit and/or receive an ultrasound beam that is generally cone-shaped as the transducer rotates with the apex of the cone being located near the face the transducer element. The chamber also includes a rotating reflector that is generally pointed proximally back toward the transducer element, which rotates about the same axis as the transducer but at a slightly different speed. The reflective face is similarly oriented off-axis to redirect the ultrasound beam outward from the device when emitting (or toward the transducer when receiving) the ultrasound beam. The difference in the velocity of their rotations causes the transducer and the reflective face to vary in and out of phase, which in turn, causes the device to actively scan a volume that is bounded interiorly by a hyperboloid and exteriorly by the effective range of the ultrasound beam.

The present disclosure encompasses multiple ways by which both the transducer and reflector may be rotated about a common axis. A first is that the device may include concentric shafts. For example, a hollow shaft holds the reflector and an interior shaft, extending through the hollow shaft, holds the transducer. The shafts are then powered by coaxially aligned rotary motors residing inside the chamber. One motor rotates the hollow shaft holding the reflector, and another motor rotates the shaft that holds the transducer. The motors may be powered by batteries residing inside the chamber, and/or by a power source residing outside the device by placing the requisite electrical connections along the length of the longitudinal member.

The transducer and reflector could also be rotated by rotary motors placed inside the chamber. Both rotary motors are coaxially aligned in particular embodiments. The shaft holding the reflector extends from a rotary motor placed farther from the control end of the device, and the shaft holding the transducer extends from a rotary motor relatively closer to the control end of the device.

The transducer and reflector could also be powered by rotary motors that reside outside the device. One embodiment of the device includes concentric shafts. For example, a hollow shaft holds the reflector and an interior shaft (through the hollow shaft) holds the transducer. Both shafts toward the control end of the device to be connected to exterior rotary motors. Examples of a flexible shaft that could extend over the length of the elongated tubular member out its proximal end include a torque coil or a torque shaft as disclosed in application Ser. No. entitled "Over-The-Wire Ultrasound System With Torque-Cable Driven Rotary Transfer," filed on even date with this application.

Another embodiment of the device that is powered by exterior rotary motors includes shafts that generally rotate next to one another over the length of the device. For example, one shaft holds the transducer inside the chamber and extends toward the control end of the device where it is connected to a rotary motor. The other shaft is connected to a gear set inside the chamber. For example, the shaft is attached to a pinion that drives a ring gear. The reflector is fixedly attached to the ring gear, and the ring gear rotates reflector about the same axis as the transducer.

The embodiments disclosed herein are intended to use ultrasound imaging to guide diagnostic or therapeutic medical procedures, including interventions. Examples of such procedures include those in the circulatory system, including IVUS procedures. Three-dimensional capability of the imaging system is considered a major advantage for use in many therapies because of the inherently three-dimensional nature of many procedures. As one example, placement of an abdominal aortic aneurysm graft requires that a guide wire be fed through the contralateral limb of the patient. The location of both the wire tip and the contralateral limb must be known and updated in real time during the placement. Such information cannot be contained in a two-dimensional image or projection, and so use of two-dimensional imaging devices require a "guess and check" method of placement, under external fluoroscopic guidance or two-dimensional ultrasound.

DETAILED DESCRIPTION OF THE ILLUSTRATED EMBODIMENTS

The principles of this disclosure are explained below using specific language to describe the example embodiments illustrated in the drawings. The reader should understand that the specific language does not limit the scope of the claims that protect subject matter as taught in this disclosure. This disclosure also includes any modifications to the illustrated embodiments plus any applications of the disclosure that would normally occur to one skilled in this area of technology.

The attached drawings generally depict multiple examples of a device 20 that can be used for internal ultrasound procedures. Such devices may be diagnostic or therapeutic (including interventional) in application, and include devices inserted percutaneously, subcutaneously or endoluminally into a patient. Examples of such devices include embodiments designed for intravascular ultrasound (IVUS) imaging or treatment.

Figure 1:
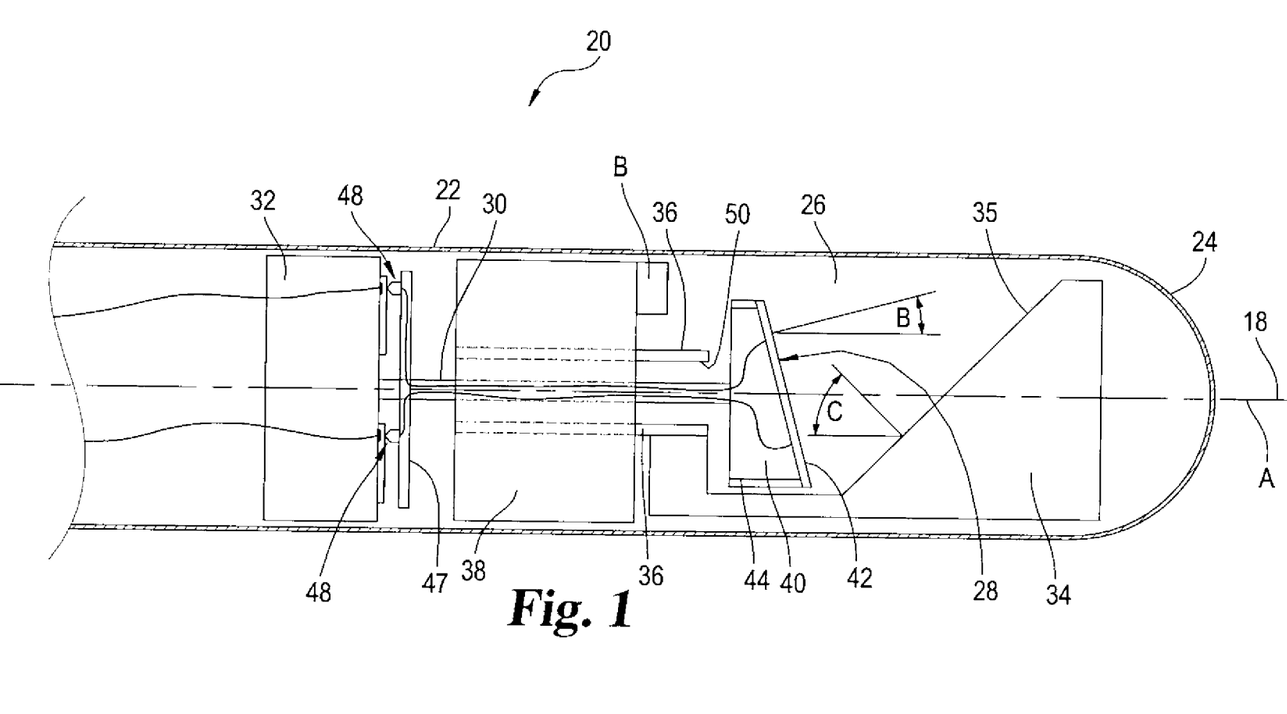
FIG. 1 is a schematic part cross-sectional side view of an embodiment of an application-end portion of a three-dimensional internal ultrasound device.

FIG. 1 illustrates the application end of an exemplary embodiment of a medical device 20, i.e., an end for insertion into the body and moving to the area of the body to be imaged or otherwise treated. Catheter or other flexible elongated or tubular member 22 has a wall 24 that defines an internal chamber 26. Catheter 22 is sized and configured to insert into a patient's arteries or veins as well as travel along a patient's vascular system. In this embodiment, chamber 26 contains a transducer 28, a shaft 30 to rotate transducer 28, and a rotary motor 32 to turn shaft 30. This embodiment also includes a reflector 34 with a reflective face 35, a hollow shaft 36 to rotate reflector 34, and a rotary motor 38 to turn hollow shaft 36. Transducer 28 and reflective face 35 are oriented generally facing each other and, as shown, are both tilted off-axis in that neither reside in a perpendicular transverse plane (also known as an axial plane) relative to longitudinal axis A of device 20. The oblique angles of the off-axis tilts allow the ultrasound waves emitted from transducer 28 to be redirected laterally by reflective face 35 outward from device 20. The oblique angles of the off-axis tilts also allow the ultrasound waves received against reflective face 35 to be redirected internally against transducer 28. Both transducer 28 and reflective face 35 are further rotatable around a common axis 18.

As will be discussed more fully below, transducer 28 and reflective face 35 are preferably, but not necessarily, configured to rotate in the same direction, but at slightly different speeds. The difference in angular velocity causes the respective rotations of transducer 28 and reflective face 35 to vary in and out of phase. As they vary in and out of phase, transducer 28 and reflective face 35 produce an ultrasound beam that traces out a three-dimensional volume that is bounded interiorly by a hyperboloid and is bounded exteriorly by the effective range of the ultrasound beam. In the illustrated embodiments, common axis 18 is also the longitudinal axis A of device 20, which provides symmetric stability. It will be understood that rotating transducer 28 and rotating reflective face 35 may also share a common axis 18 that is independent of the overall longitudinal axis of device 20. In other words, it is also contemplated that common axis 18 could be offset and/or non-parallel from the longitudinal axis of device 20 as well as reside at an oblique angle relative to the longitudinal axis of device 20.

Catheter 22 in the illustrated embodiment is an elongated device of plastic or other sturdy flexible material that presents a barrier to the passage of ultrasound signals (i.e. the difference in acoustic impedance at the boundary of the material and the substances adjacent it) sufficiently small that ultrasound images may be reasonably acquired through the barrier. For example, when used within a blood vessel containing body tissues and blood, it is preferable for catheter 22 to be at least partially (for example, in and adjacent to wall 24) constructed of a material that has acoustic impedance(s) similar to that of body fluids such as blood. In some embodiments, only the end of catheter 22 adjacent transducer 28 and reflector 34 (for example, wall 24) will be acoustically transparent, but it is understood that more or all of catheter 22 may be made of the same material as wall 24 in some embodiments. Possible materials could include, for example, a polymer material such as polyethylene (PE), polymethylpentene (PMP), or acrylonitrile butathene styrene (ABS). One possible preferred thickness of at least the portion of wall 24 or catheter 22 which serves as the viewing window is approximately ½ of the wavelength corresponding to center frequency of the ultrasound beam, although other thicknesses may be used.

Wall 24 surrounds chamber 26, which is at the tip of the application end of device 20 in the illustrated embodiment, and extends toward the physician operating device 20, e.g. toward a control end or portion of device 20. Wall 24 and/or catheter 22 may extend toward the control end to a location outside of the patient during use, and may end in a handle or other operating portion (not shown). Particular embodiments of catheter 22 or at least chamber 26 are cylindrical, and are sized for insertion into and passage through blood vessels, such as insertion into the femoral artery and passage through it toward the heart.

Transducer 28 is indicated schematically in the drawings. The term "transducer" should be understood to include an assembly of two or more parts as well as a single piece. It will further be understood that "transducer" as used herein includes devices that transmit ultrasound (that is, transform an electrical (RF) signal to ultrasound), receive ultrasound (that is, transform ultrasound to an electrical (RF) signal), or both. If multiple transducers or pieces are provided, transmission of ultrasound may occur at one and reception at another. Transducer(s) as described herein may have one or more piezoelectric elements as respective transducers, and may operate in combination with other transducers within or outside the body.

An exemplary transducer 28 includes a body or backing layer 40 with a transducer element 42 attached to one side of body 40, and one or more clamping rings 44. An impedance matching layer (not shown) may also be attached to transducer element 42, for example, opposite body 40. Body 40 may substantially absorb ultrasound signals, so that such signals are effectively projected only in one general direction outward from element 42, for example, to one side generally opposite body 40 or in a limited angular range radially from body 40. Clamping rings 44 have been determined to improve efficiency and the mechanical stability of transducer 28. Transducer 28 is capable of sending and receiving ultrasound waves in a range of frequencies which are typically used in medical ultrasound procedures, such as, for example, in the range from 2 MHz to 50 MHz.

Transducer 28 is electronically connected to a power source and to an imaging system. Examples of connections include conductors (e.g. wires or cables) along wall 24, or via slip ring and brush assembly, items 47 and 48 (FIG.1), and/or via metallic film(s) along wall 24. Embodiments of examples are discussed and shown in Application Ser. Nos. 61/713,143 (entitled "Feedback/Registration Mechanism for Ultrasound Devices" and filed on Oct. 12, 2012) and 61/713,186 (entitled "Mechanical Scanning Ultrasound Transducer with Micromotor" and filed on Oct. 12, 2012), each of which is incorporated by reference herein in its entirety.

In the particular embodiment shown in FIG. 1, transducer 28 is mounted on shaft 30. Shaft 30 is mechanically connected or integral to a rotating shaft within rotary motor 32. Shaft 30 is connected to transducer 28 by interference or similar fit or by other fixed attachment (for example by adhesive, solder or welding). Rotary motor 32 is configured in some embodiments to rotate shaft 30 continuously in a single rotational direction, and transducer 28 is rotated around the rotating axis of shaft 30 in the same rotational direction. One or more of the back EMF, the ultrasound signal emitted and/or received by transducer 28, and motor saliency can be used as a feedback mechanism to precisely control the rotational position of rotary motor 32 (and transducer 28 rotated by it) relative to the rest of device 20, ensuring proper registration of images obtained through transducer 28. Registration can also or alternatively be accomplished via methods and structures discussed in Application Ser. No. 61/713,143 entitled "Feedback/Registration Mechanism for Ultrasound Devices" and filed on Oct. 12, 2012, which is incorporated by reference herein in its entirety.

Reflector 34 is configured to reflect or otherwise redirect an ultrasound signal from transducer 28 outward from device 20. Reflector 34 is also configured to reflect or otherwise redirect an ultrasound signal toward transducer 28 upon returning to device 20. Reflector 34 includes a reflective face 35. Reflective face 35 is preferably constructed as a smooth surface in order to minimize scattering of the ultrasound signal that would occur during reflection. In the present example, the reflection surface is an elliptical disc proportioned so that when viewed along common axis 18 (e.g. axis A), it appears generally circular because of its orientation with respect to the common axis 18. The elliptical design generally assists in maximizing the reflection of the ultrasound beam while minimizing the distortion of the ultrasound beam from transducer 28, providing improved image quality in most imaging applications. The reflective face 35 may be integral to reflector 34. Alternatively, the reflector 34 can include a substrate or similar structure, which includes a coated surface or layered material that includes reflective face 35. By way of example, reflective face 35 may be metal, a mirror, or similar reflective material attached to reflector 34. As a result, reflector 34 can be generally comprised of any of a variety of materials such as metal, ceramic, or a polymer or any other material which provides adequate reflection characteristics due to sufficiently varied acoustic impedance between the reflective face 35 and the acoustic impedance of the surrounding environment.

Reflector 34 is mechanically connected to or integral with hollow shaft 36, and hollow shaft 36 is mechanically connected to or integral with a rotating shaft of rotary motor 38. Hollow shaft 36 at least partially defines a lumen 50 therethrough in the particular embodiment shown in FIG. 1, which extends through the entirety of motor 38. Lumen 50 permits shaft 30 to pass through rotary motor 38, and in doing so, lumen 50 also permits shaft 30 to be coaxially aligned with hollow shaft 36. Lumen 50 still further permits transducer 28 to reside both distal to rotary motors 32 and 38 while remaining proximal to reflector 34.

Rotary motors 32 and/or 38 are microminiature motors in particular embodiments suitable for containment within chamber 26 of catheter 22, and can be powered by a source external to device 20 or powered by a source internal to device 20 such as a battery. Examples of such microminiature motors include piezoelectric or electromagnetic motors of a size and configuration suitable for containment within chamber 26 may be used. For example, a particular embodiment of rotary motor 32 or 38 is a three-phase, coreless, brushless DC electromagnetic motor, which has few components, small size and minimal complexity. In other examples, a piezoelectric microminiature motor may be used for its advantage of not requiring a gearhead (mechanical transmission) to achieve high torque, and to eliminate problems with torque cables and rotary transformers. Rotary motors 32 and 38 have a diameter in the range of 0.3 mm to 4 mm in particular embodiments, for example approximately 2.0 mm. In this regard, it is also contemplated that rotary 32 and rotary motor 38 could be physically combined into one motor with two output shafts. Such a combination would allow the overall size of the motor to be smaller by eliminating duplicative structures that would otherwise exist in two physically separate motors.

There are, in general, four aspects that allow device 20 to actively scan a three-dimensional radial volume. A first of these aspects is that transducer 28 and reflector 34 are configured to emit an ultrasound beam off of or away from common axis 18 (and/or are configured to receive an ultrasound beam toward common axis 18). Transducer element 42 is aimed generally away from the control end of device 20 and toward reflective face 35, and reflective face 35 is aimed generally toward transducer element 42. In the embodiment depicted in FIG. 1, reflective face 35 is also mounted off-axis about 45 degrees (angle C) from residing within a perpendicular transverse plane (also known as an axial plane) relative to common axis 18. When transducer element 42 emits an ultrasound beam toward reflector 34, the oblique angle of reflective face 35 redirects the beam outward or away from common axis 18. (Similarly, when device 20 receives an ultrasound beam, the oblique angle of reflective face 35 redirects the beam toward transducer element 42.)

A second of these aspects is that transducer 28 and reflector 34 are configured to rotate an ultrasound beam around common axis 18. When power is applied to rotary motor 38, rotary motor 38 applies torque to hollow shaft 36, which causes reflective face 35 to rotate. When transducer element 42 emits an ultrasound beam toward rotating reflector 34, rotating reflective face 35 not only redirects the beam outward or away from common axis 18, but also rotates the ultrasound beam around common axis 18 as reflective face 35 rotates. (Similarly, transducer element 42 may also receive a beam redirected by reflective face 35 as reflective face 35 rotates.)

A third of these aspects is that transducer 28 and reflective face 35 are configured to conically emit or broadcast an ultrasound beam from reflective face 35. In the embodiment depicted in FIG. 1, transducer element 42 is mounted off-axis about 15 degrees (angle B) from residing within a perpendicular transverse plane relative to common axis 18. When power is applied to rotary motor 32, rotary motor 32 applies torque to shaft 30, causing shaft 30 and transducer element 42 to rotate. The off-axis transducer element 42 emits an ultrasound beam that is generally cone-shaped as transducer element 42 rotates (the apex of the cone being located at or near transducer element 42). When rotating transducer element 42 emits an ultrasound beam toward reflector 34, the oblique angle of rotating transducer element 42 varies the angle of incidence of the ultrasound beam upon reflective face 35. In general, a change in the angle of incidence upon reflective face 35 causes an equal change of reflection of the ultrasound beam away from reflective face 35. Hence, the ultrasound beam reflected from reflective face 35 generally assumes a similar shape as the ultrasound beam emitted from transducer element 42, which here is cone-shaped. A returning beam is similarly reflected by reflective face 35 back toward transducer element 42.

A fourth aspect is that transducer 28 and reflector 34 are rotated about common axis 18 at slightly different speeds. The speed differential allows rotating transducer element 42 and rotating reflective face 35 to vary in and out of phase. That phase shift combined with the general axial rotation of the ultrasound beam around central axis 18, discussed above, results in an ultrasound beam emanating from device 20 that is bounded exteriorly by the effective range of the beam and bounded interiorly by a hyperboloid. The phase shift and the general rotation around central axis 18 also allow device 20 to receive an ultrasound scan of the same volume.

The ultrasound beam emanating from the embodiment depicted in FIG. 1, sweeps 15 degrees ahead and 15 degrees behind a perpendicular transverse plane relative to common axis 18. One could obtain a wider sweep by using a larger transducer off-axis tilt (that is, a larger oblique angle B), provided that the incident ultrasound beam remains focused on reflective face 35 throughout most, if not all, of the rotations of transducer 28 and reflector 34. Similarly, the off-axis tilt (oblique angle A) of reflective face 35 may also be chosen to create an ultrasound beam sweep that is angled more forward or rearward.

While constant rotational velocities may be preferable in most applications, it is further contemplated that non-constant rotational velocities for both reflector 34 and transducer 28 could be used to practice the principles of this invention. The non-constant velocities could be used to sweep arbitrary paths in three-dimensional space. This could be used, for example, to image only a desired region of interest or to ensure a uniform sampling density. It could also be used for more complex beam control such as to sample a region of interest at a high frame rate and other parts at a low frame rate.

Figure 2:
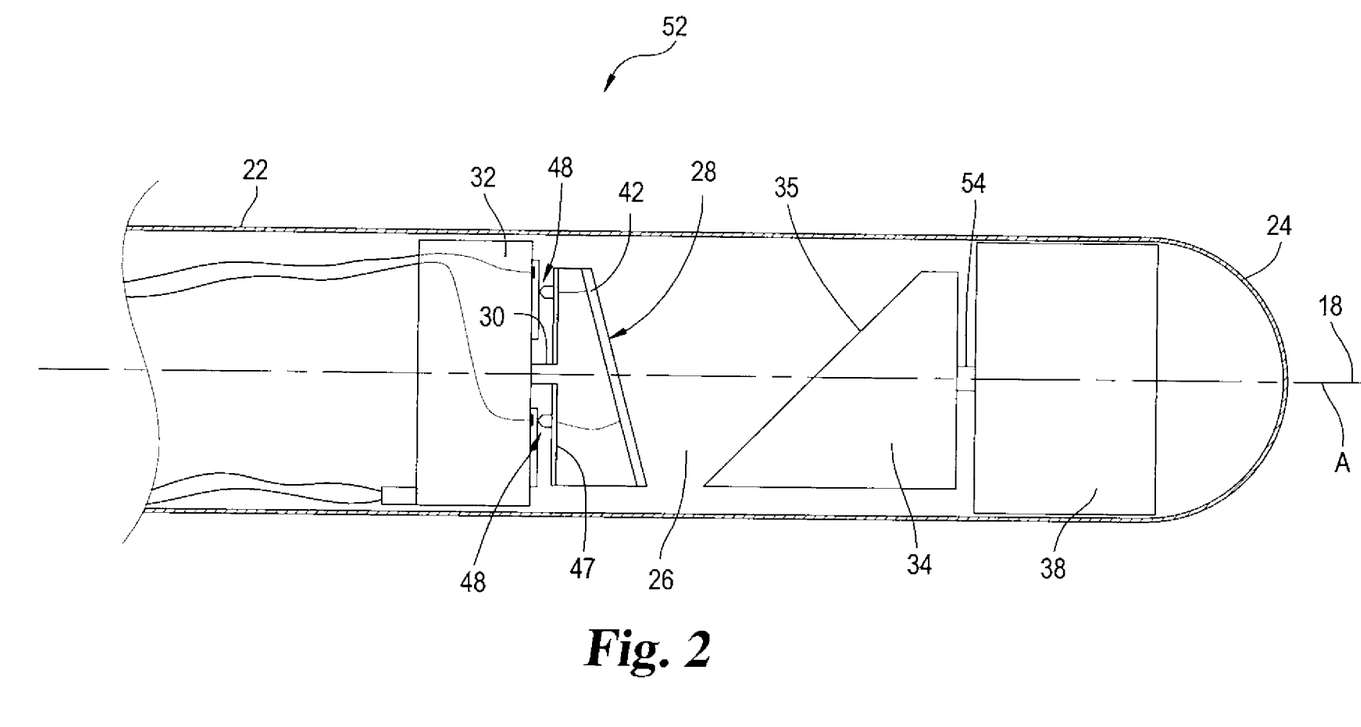
FIG. 2 is a schematic part cross-sectional side view of another embodiment of an application-end portion of a three-dimensional internal ultrasound device.

Device 52, depicted in FIG. 2, is another embodiment that incorporates the principals of the disclosure. Similar to device 20 depicted in FIG. 1, device 52 is a catheter or other flexible elongated or tubular member 22 with a wall 24 that defines an internal chamber 26 and is generally the same size and made of the same material as device 20. Chamber 26 contains transducer 28, shaft 30 to rotate transducer 28, and rotary motor 32 to turn shaft 30. Chamber 26 also contains reflector 34, with reflective face 35, a shaft 54 to rotate reflector 34, and rotary motor 38 to turn shaft 54. Transducer 28 and reflective face 35 are oriented facing each other and both are tilted off-axis, substantially as described above. Electrical connections for transducer 28 are similar or identical to those described and shown with respect to FIG. 1, e.g. a slip ring and brush assembly 47, 48. Other examples as noted above may be used with or in place of such connections.

One of the differences between device 20 (FIG. 1) and device 52 (FIG. 2), however, is that rotary motor 38 is located distal (i.e. further from the control end of device 20) to both transducer 28 and reflector 34, near the tip of catheter 22. Such positioning allows transducer 28 to be coaxial with reflector 34 without using a hollow shaft or passing a shaft through rotary motor 32. The wiring (not shown) to operate motor 38 may run along or within wall 24, e.g. through the imaging window of device 52. One method to do this is to apply coating(s) of gold or other conductive materials to the surface of the window as discussed in U.S. application Ser. No. 14/051,846 (entitled "Feedback/Registration Mechanism for Ultrasound Devices"), which was filed on Oct. 11, 2013, the disclosure of which is incorporated herein by reference it its entirety. The coating(s) may be isolated from fluids by placing an insulating layer over the coating(s). Alternatively, rotary motor 38 is powered by a battery (not shown), e.g. with a microcontroller (not shown), which are activated at the time of an ultrasound procedure. As the catheter is generally disposed after use, the battery need only last as long as the ultrasound procedure.

Figure 3:
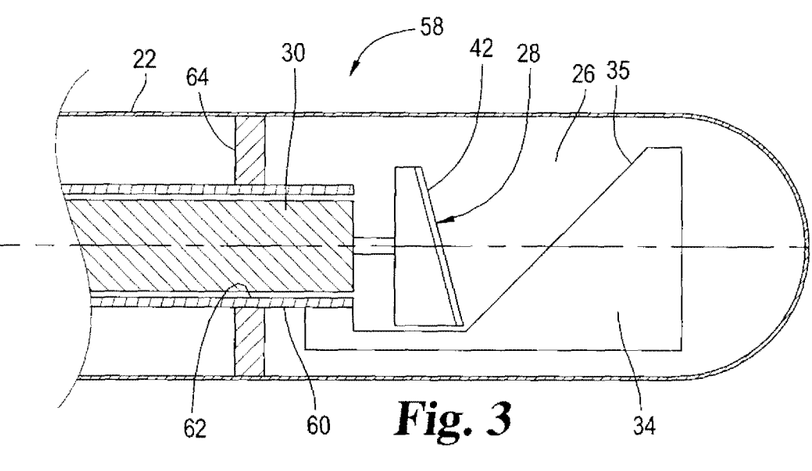
FIG. 3 is a schematic part cross-sectional side view of another embodiment of an application-end portion of a three-dimensional internal ultrasound device.

Device 58, depicted in FIG. 3, is another embodiment that incorporates the principals of the disclosure. Similar to device 20 depicted in FIG. 1, device 58 is a catheter or other flexible elongated or tubular member 22 with a wall 24 that defines an internal chamber 26 and is generally the same size and made of the same material as device 20. Chamber 26 contains transducer 28 and shaft 30 to rotate transducer 28. Chamber 26 also contains reflector 34, with reflective face 35, and a shaft 60 to rotate reflector 34. Transducer 28 and reflective face 35 are oriented facing each other and both are tilted off-axis, substantially as described previously. Electrical connections for transducer 28 (not shown for clarity) are similar or identical to those described and shown in FIG. 1, e.g. a slip ring and brush assembly. The slip disk mechanism or assembly could be built into a handle of the device and wiring extending from it may run distally to transducer 28 through member 22, or may extend along (e.g. be fixed to) shaft 30. Alternatively, the slip disk mechanism or assembly could be mounted near the transducer and stationary wiring (e.g. wire(s) or metallic film(s)) may extend along the inside of member 22. Other examples as noted above may be used with or in place of such connections.

One of the differences between device 20 (FIG. 1) and device 58 (FIG. 3) is that shaft 30 and shaft 60 extend from chamber 26 and extend outside the patient during use. The control end (not shown) terminates in a handle or other operating portion (not shown) that contains the motors to rotate shaft 30 and shaft 60. In this embodiment, shaft 30 and shaft 60 are comprised of torque coils with shaft 30 residing inside shaft 60. The internal surface 62 of shaft 60 generally supports the radial load of shaft 30 as shaft 30 rotates, and a bushing 64 supports the radial load of shaft 60 as shaft 60 rotates.

Figure 3A:
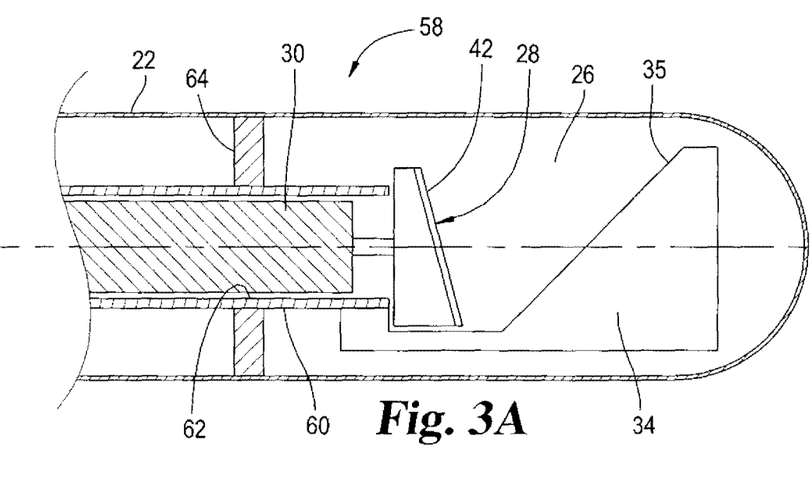
FIG. 3A is a schematic part cross-sectional side view of an embodiment as in FIG. 3.
Figure 3B:
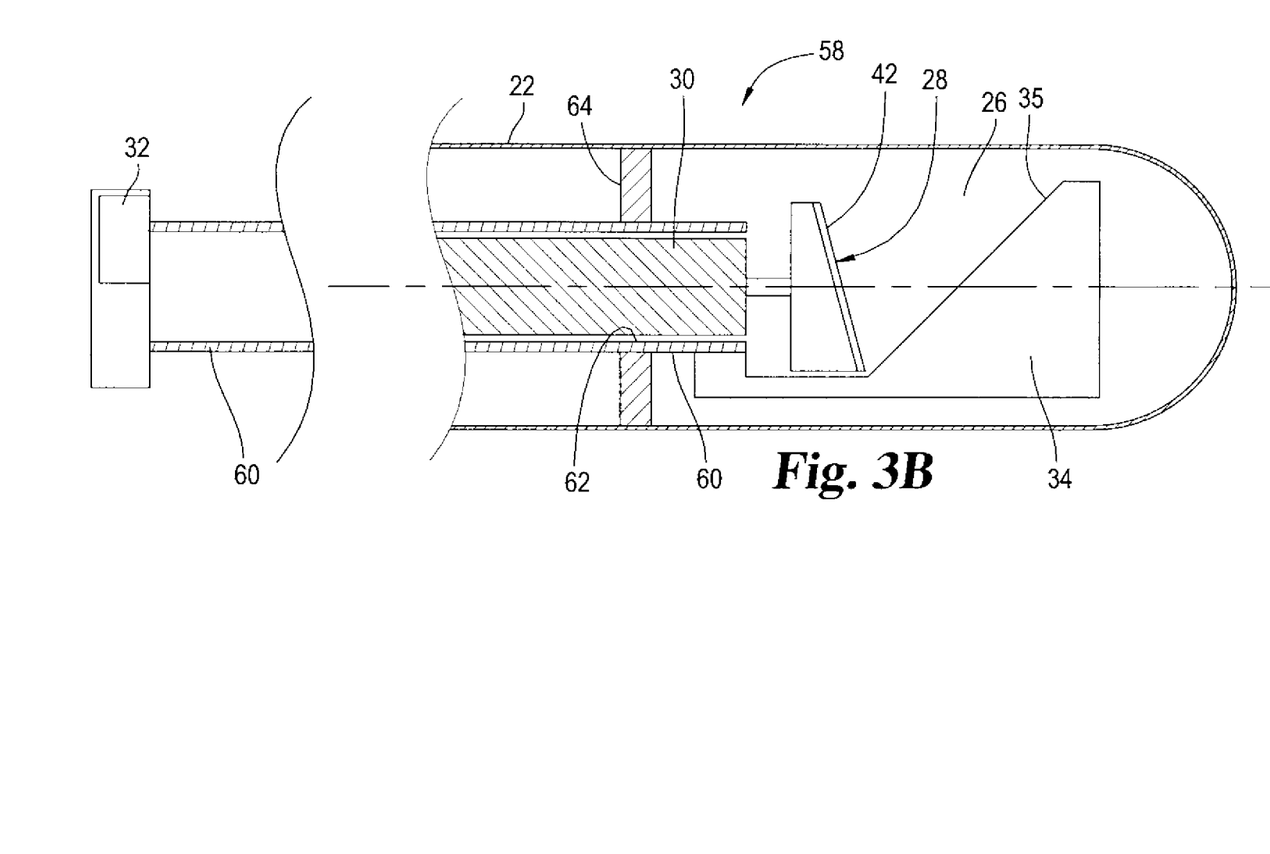
FIG. 3B is a schematic part cross-sectional side view of an embodiment as in FIG. 3.

Embodiments as disclosed herein may also have a longitudinal motion capability in order to expand or vary the length and/or volume of the space imaged. For example, FIG. 3A shows an embodiment as in FIG. 3, in which rotating reflector 34 is movable longitudinally, i.e. along axis A. Specifically, FIG. 3A shows reflector 34 in a position forward of that shown in FIG. 3, yet not contacting wall 24. Shaft 60 is movable longitudinally through bushing 64, preferably while maintaining a seal with bushing 64. A portion of shaft 60 extending toward the operator, or a driving shaft, torque coins), or other turning mechanism connected to shaft 60, can be translated toward or away from the tip of the application end of device 20. In doing so, shaft 60 pushes or pulls the arm of rotating mirror 34, causing the reflective surface 35 to move toward or away from transducer 28, e.g. to and between the positions seen in FIGS. 3 and 3A. In so doing, the angles of reflection of the ultrasound beam may be changed, and the length of the imaged area may be increased or decreased, as the operator desires. In such embodiments, mirror 34 and transducer are moved relative to each other longitudinally, even if transducer 28 remains longitudinally stationary with respect to member 22.

Figure 4:
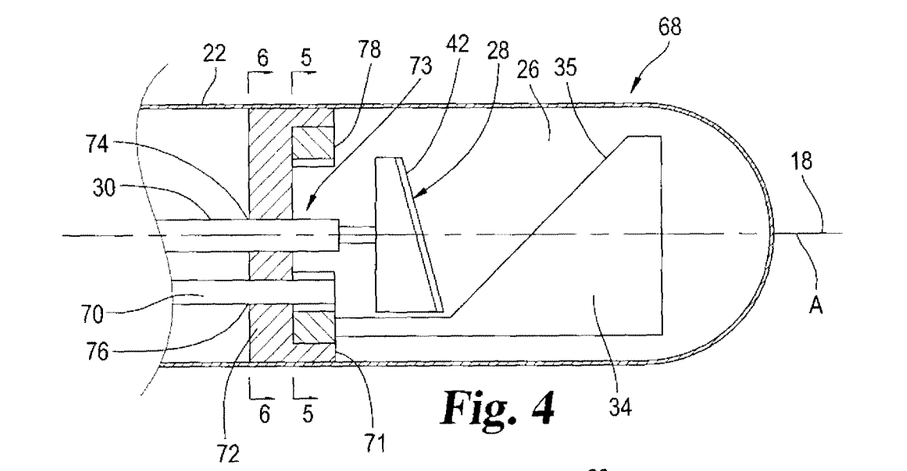
FIG. 4 is a schematic part cross-sectional side view of another embodiment of an application-end portion of a three-dimensional internal ultrasound device.

Device 68, depicted in FIG. 4, is yet another embodiment that incorporates the principals of the disclosure. Similar to device 20 depicted in FIG. 1, device 68 is a catheter or other flexible elongated or tubular member 22 with a wall 24 that defines an internal chamber 26 and is generally the same size and made of the same material as device 20 (FIG. 1). Chamber 26 in FIG. 4 contains transducer 28 and shaft 30 to rotate transducer 28. Chamber 26 also contains reflector 34, with reflective face 35, and a shaft 70 to rotate reflector 34. Transducer 28 and reflective face 35 are oriented facing each other and both are tilted off-axis, substantially as described above. Electrical connections for transducer 28 (not shown for clarity) are similar or identical to those described and shown in FIG. 1, e.g. a slip ring and brush assembly. The slip disk mechanism or assembly could be built into a handle of the device and wiring extending from it may run distally to transducer 28 through member 22, or may extend along (e.g. be fixed to) shaft 30. Alternatively, the slip disk mechanism or assembly could be mounted near the transducer and stationary wiring (e.g. wire(s) or metallic film(s)) may extend along the inside of member 22. Other examples as noted above may be used with or in place of such connections.

Figure 6:
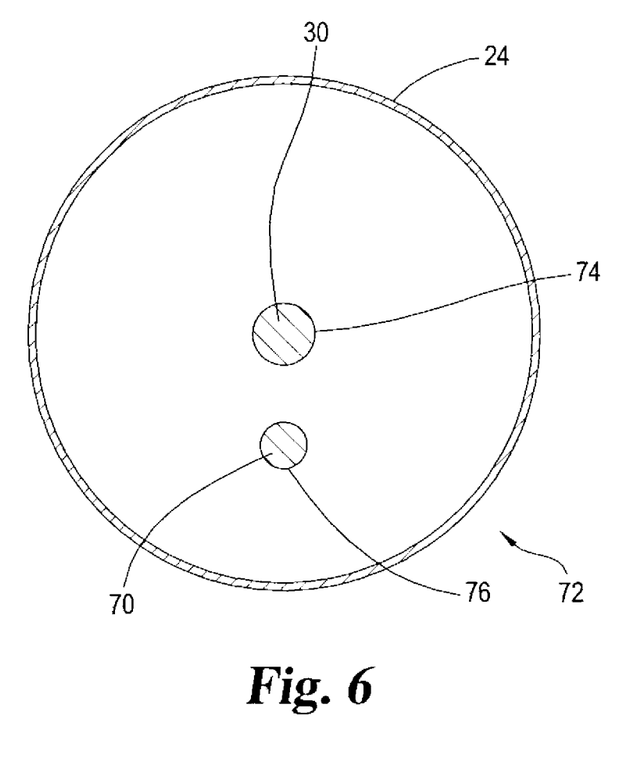
FIG. 6 is a schematic part cross-sectional end view of the bushing utilized in the embodiment depicted in FIG. 4, taken along the lines 6-6 in FIG. 4 and viewed in the direction of the arrows.

One of the differences between device 20 (FIG. 1) and device 68 (FIG. 4) is that shaft 30 and shaft 70 extend from chamber 26 and extend outside the patient during use. The control end (not shown) terminates in a handle or other operating portion (not shown) that contains the motors to rotate shaft 30 and shaft 70. In this embodiment, shaft 30 and shaft 70 are comprised of two torque coils that generally reside next to each other inside catheter 22. The radial load of both shaft 30 and shaft 70 are generally supported by bushing 72 with an opening 74 (FIG. 6) therethrough to support the distal end of shaft 30 and an opening 76 (FIG. 6) therethrough to support the distal end of shaft 70.

Figure 5:
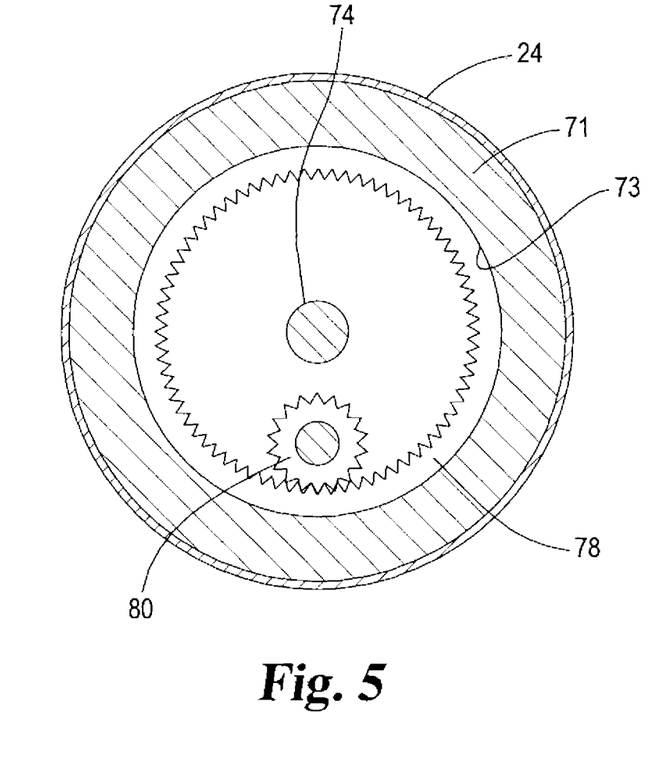
FIG. 5 is a schematic part cross-sectional end view of the ring and pinion gear utilized in the embodiment depicted in FIG. 4, taken along the lines 5-5 in FIG. 4 and viewed in the direction of the arrows.

Referring to both FIGS. 4 and 5, reflector 34 is rotated in device 68 by input pinion 80 that rotates ring gear 78. Bushing 72 generally includes a chamber 73 that is radially defined by fixed edge 71 that distally extends from the face of bushing 72. Chamber 73 carries movable ring gear 78 and fixed edge 71 supports the radial load of ring gear 78. Reflector 34 is fixedly secured to ring gear 78. Pinion 80 is securely attached or integral to the distal end of shaft 70 and pinion 80 is located to mechanically connect (mesh) with the internal teeth of ring gear 78. When shaft 70 turns, pinion 80 rotates which, in turn, causes ring gear 78 and reflector 34 to rotate about central axis 18.

Figure 4A:
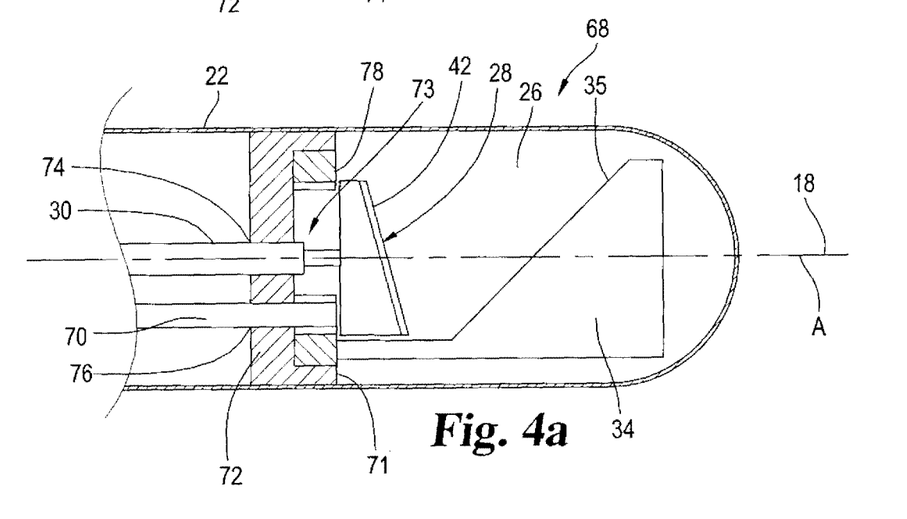
FIG. 4A is a schematic part cross-sectional side view of an embodiment as in FIG. 4.

As generally described above with respect to FIG. 3A, an embodiment of FIG. 4 is shown in which reflector 34 is movable longitudinally in a similar manner (FIG. 4A). Bushing 72 may remain fixed in particular embodiments, with shaft 70 and/or ring gear 78 moving toward or away from the application end of device 20. In other embodiments, bushing 72 may move with shaft 70 and ring gear 78 around shaft 30, so that mirror 34 moves relative to transducer 28.

An example of using device 20 (FIG. 1) in an IVUS procedure follows. As previously noted, the devices disclosed herein may also be used in other types of internal procedures.

Device 20 is inserted into a blood vessel of a patient and maneuvered to a desired location within the vasculature. Transducer 28 may be operated during travel to the desired location. Throughout placement and at a desired imaging location, rotary motor 32 and 38 can be operated to provide real-time three-dimensional images around device 20. Controls for motors 32 and/or 38 (not shown) may be provided to maintain one or both at a particular rotational speed or pattern, and thereby to image one or more desired areas for a desired display.

Embodiments of device 20 used in IVUS would preferably be about 2.7-3.0 mm or less in diameter, so as to be effective in the human vasculature. Rotary motors 32 and 38 each may have a length of approximately 2.5 mm in particular embodiments. With reflector 34 and transducer (piezoelectric element) 28 included, an overall length may be approximately 10 mm. While device 20 is described in part above in the context of intravascular (IVUS) uses, it will be understood that embodiments of device 20 could also be used for other medical procedures and/or with a variety of other medical devices. The versatility of the embodiments described herein allows IVUS to be used to guide percutaneous therapeutic interventions such as for example embolism coils, stents, filters, graphs, balloons, biopsies, and administering therapeutics, etc. Device 20 can be used to locate various anatomical landmarks that will be used to correctly place or guided therapy. Typical landmarks include confluences, bifurcations, side branches, nearby vessels, nearby nerves, the heart, and other tissues adjacent to vessels or other orifices containing the IVUS transducer. Device 20 can also be used to locate diseased tissue that will be treated or avoided. Device 20 can be used during a biopsy to provide an image of a needle being deployed into tissue. During a TIPS (transjugular intrahepating portosystemic shunt) procedure an image can be produced to allow a physician to watch a needle being placed into the portal vein. Device 20 can allow a physician to place a guide wire into a contralateral leg. Device 20 could also be used to image the location of a deployed implantable device both during and after deployment.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. It will be understood that features or attributes noted with respect to one or more specific embodiments may be used or incorporated into other embodiments of the structures and methods disclosed.

What is claimed is:

1. An apparatus for ultrasound procedures, comprising:
an elongated tubular member with a control end, an application portion, and a chamber within the application portion;
a transducer with a transducer element to at least one of emit and receive at least one ultrasound beam, said transducer residing within the chamber of said elongated tubular member;
a reflector with a reflective face, said reflector residing within the chamber of said elongated tubular member, and
wherein said transducer and said reflector are rotatable around a common longitudinal axis; wherein the transducer element of said transducer is oriented at a first constant oblique angle to the common longitudinal axis; and wherein the reflective face of said reflector is oriented at a second constant oblique angle to the common longitudinal axis, said oblique angles allowing ultrasound to be at least one of (a) redirected laterally by the reflective face outward from the chamber and (b) redirected internally by the reflective face to the transducer.

2. The apparatus of claim 1, wherein the transducer element of said transducer is at least partially aimed toward the reflective face of said reflector.

3. The apparatus of claim 1, wherein the reflective face of said reflector is at least partially aimed toward the transducer element of said transducer.

4. The apparatus of claim 1, further comprising a first shaft, said first shaft operationally connected to said transducer to rotate said transducer around the common longitudinal axis.

5. The apparatus of claim 4, further comprising a second shaft, said second shaft operationally connected to said reflector to rotate said reflector around the common longitudinal axis, wherein said second shaft is hollow and with open ends forming a lumen therethrough, and wherein said first shaft is positioned within the lumen of said second shaft.

6. The apparatus of claim 5, further comprising a microminiature motor residing within the chamber of said elongated tubular member, and said microminiature motor is operationally connected to said second shaft.

7. The apparatus of claim 6, further comprising a battery electrically connected to said microminiature motor and said battery resides within the chamber of said elongated tubular member.

8. The apparatus of claim 4, further comprising a microminiature motor residing within the chamber of said elongated tubular member, and said microminiature motor is operationally connected to said first shaft.

9. The apparatus of claim 4, further comprising an external motor, wherein said first shaft extends toward said external motor and wherein said external motor is operationally connected to said first shaft.

10. The apparatus of claim 1, further comprising a shaft, said shaft operationally connected to said reflector to rotate said reflector around the common longitudinal axis.

11. The apparatus of claim 10, further comprising a microminiature motor residing within the chamber of said elongated tubular member, and said microminiature motor is operationally connected to said shaft.

12. The apparatus of claim 11, wherein said microminiature motor is located at a position further from the control end than the reflective face of said reflector.

13. The apparatus of claim 11, further comprising a battery electrically connected to said microminiature motor and said battery resides within the chamber of said elongated tubular member.

14. The apparatus of claim 10, further comprising an external motor, wherein said shaft extends toward said external motor and wherein said external motor is operationally connected to said shaft.

15. The apparatus of claim 1, wherein said transducer is rotatable at a first speed, wherein said reflector is simultaneously rotatable at a second speed, and wherein the first speed is not equal to the second speed.

16. The apparatus of claim 15, wherein said transducer and said reflector rotate in the same direction.

17. The apparatus of claim 1, wherein said elongated tubular member is a catheter with an interior lumen.

18. The apparatus of claim 17, further comprising a battery electrically connected to a microminiature motor and said battery resides within the chamber of said elongated tubular member.

19. The apparatus of claim 1, wherein the reflector is movable with respect to the transducer in a direction parallel to the longitudinal axis.

20. The apparatus of claim 1, wherein the transducer and reflective face are configured to emit an ultrasound beam from the reflective face in the shape of a cone having an apex at or near the transducer.

21. The apparatus of claim 1, wherein an ultrasound beam emanating from the apparatus sweeps a sweep angle ahead of and behind a perpendicular transverse plane relative to the common longitudinal axis, and wherein the sweep angle is equal to the first oblique angle.

22. An apparatus for ultrasound procedures, comprising:
an elongated tubular member with a control end, an application portion, and a chamber within the application portion;
a transducer with a transducer element to at least one of emit and receive at least one ultrasound beam, said transducer residing within the chamber of said elongated tubular member; and
a reflector with a reflective face, said reflector residing within the chamber of said elongated tubular member,
wherein said transducer is rotatable at a first speed, wherein said reflector is simultaneously rotatable at a second speed, and wherein the first speed is not equal to the second speed, and wherein said transducer and said reflector are oriented at respective oblique angles with respect to a longitudinal axis, the angles allowing ultrasound to be at least one of (a) redirected laterally by the reflective face outward from the chamber and (b) redirected internally by the reflective face to the transducer.

23. The apparatus of claim 22, wherein said transducer and said reflector rotate in the same direction.

24. The catheter of claim 23, wherein said second shaft is hollow with open ends forming a lumen therethrough, and wherein said first shaft is positioned within the lumen of said second shaft.

25. The apparatus of claim 22, wherein said elongated tubular member is a catheter with an interior lumen.

26. The apparatus of claim 22, wherein the reflector is movable with respect to the transducer in a direction parallel to an axis around which the reflector is rotatable.

27. The apparatus of claim 22, wherein the respective oblique angles are constant.

28. The apparatus of claim 22, wherein the transducer and reflective face are configured to emit an ultrasound beam from the reflective face in the shape of a cone having an apex at or near the transducer.

29. The apparatus of claim 22, wherein an ultrasound beam emanating from the apparatus sweeps a sweep angle ahead of and behind a perpendicular transverse plane relative to the common longitudinal axis, and wherein the sweep angle is equal to the oblique angle of the transducer.

* * * * *

UNITED STATES PATENT AND TRADEMARK OFFICE
CERTIFICATE OF CORRECTION

PATENT NO.        : 10,695,026 B2                                          Page 1 of 1
APPLICATION NO.   : 15/235217
DATED             : June 30, 2020
INVENTOR(S)       : William J. Havel et al.

It is certified that error appears in the above-identified patent and that said Letters Patent is hereby corrected as shown below:

In the Specification

Column 4, Lines 48-49, delete "butathene" replace with –butadiene–

Column 9, Line 22, delete "coins" replace with –coil(s)–

Signed and Sealed this
Tenth Day of November, 2020

Andrei Iancu
*Director of the United States Patent and Trademark Office*